United States Patent [19]

Kato et al.

[11] Patent Number: 4,981,125
[45] Date of Patent: Jan. 1, 1991

[54] OUTPUT CORRECTION METHOD FOR EXHAUST GAS INGREDIENT-CONCENTRATION SENSORS OF PROPORTIONAL-OUTPUT TYPE

[75] Inventors: Akira Kato; Toru Yano; Yasuhiro Toyoda, all of Wako, Japan

[73] Assignee: Honda Giken Kogyo K.K., Tokyo, Japan

[21] Appl. No.: 370,277

[22] Filed: Jun. 22, 1989

[30] Foreign Application Priority Data

Jun. 30, 1988 [JP] Japan .................................. 63-162854

[51] Int. Cl.⁵ ...................... G01N 27/409; F02M 7/00
[52] U.S. Cl. .................................... 123/440; 123/489; 204/153.18; 204/401; 204/406
[58] Field of Search ........................ 204/15, 406, 401; 123/489, 440

[56] References Cited

U.S. PATENT DOCUMENTS

| | | | |
|---|---|---|---|
| 4,770,758 | 9/1988 | Suzuki et al. | 204/406 |
| 4,777,922 | 10/1988 | Mieno et al. | 123/479 |
| 4,796,587 | 1/1989 | Nakajima et al. | 123/440 |
| 4,841,934 | 6/1989 | Logothetis et al. | 123/440 |

FOREIGN PATENT DOCUMENTS 120354 8/1985 Japan .
198744 9/1987 Japan .

*Primary Examiner*—G. L. Kaplan
*Attorney, Agent, or Firm*—Arthur L. Lessler

[57] ABSTRACT

An output correction method for a proportional-output type $O_2$ sensor including an oxygen concentration detecting element formed by an oxygen-pumping element and a cell element, each of the oxygen-pumping element and the cell element being composed of a wall of a solid electrolytic material having oxygen ion-conductivity, and a pair of electrodes having the wall interposed therebetween. The oxgen-pumping element is supplied with an output voltage corresponding to a difference between a voltage developed between the electrodes of the cell element and a predetermined reference voltage, and current flowing in the oxygen-pumping element is detected. A correction resistance supplies information indicative of a deviation of an air-fuel ratio detected by the sensor with respect to a predetermined reference air-fuel ratio. A correction value is determined on the basis of the information and the direction of flow of the current. The detected current is corrected by the use of the determined corrected value. A desired air-fuel ratio is calculated on the basis of the corrected current.

4 Claims, 5 Drawing Sheets

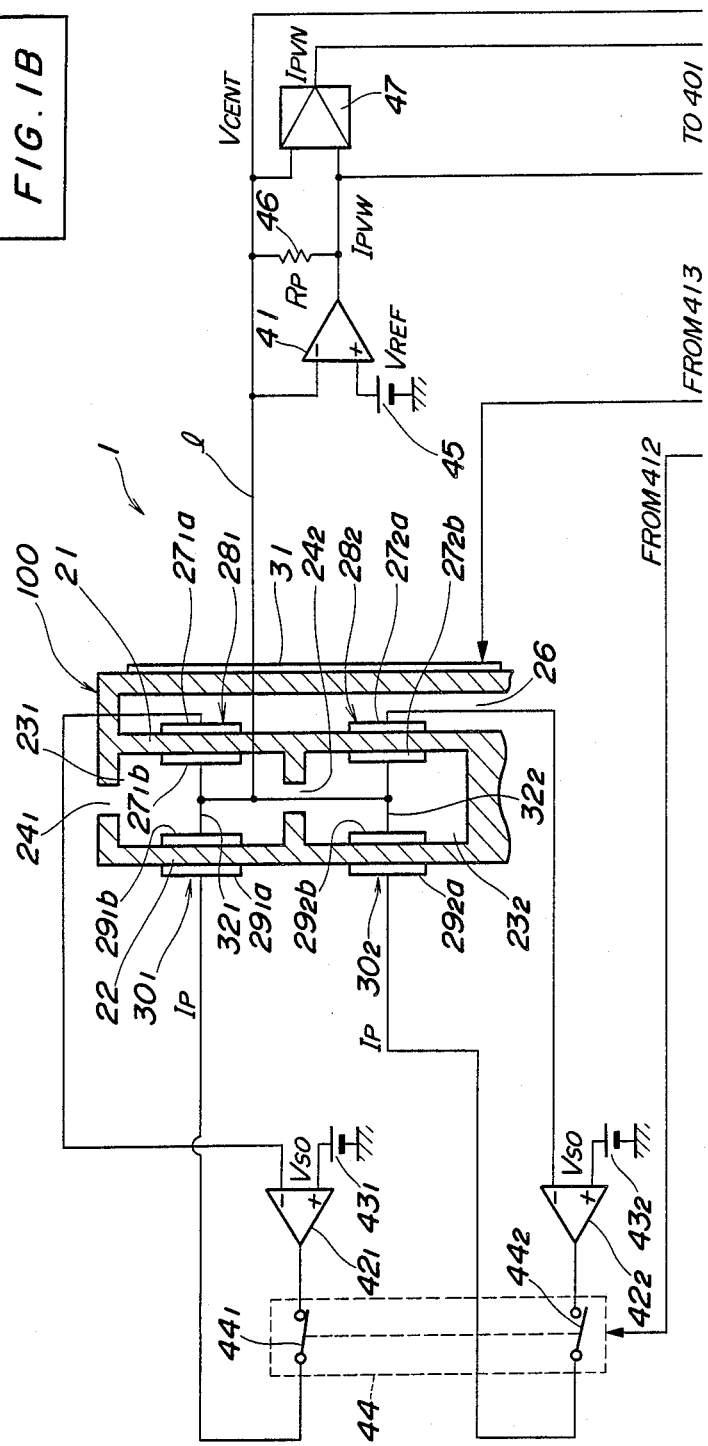

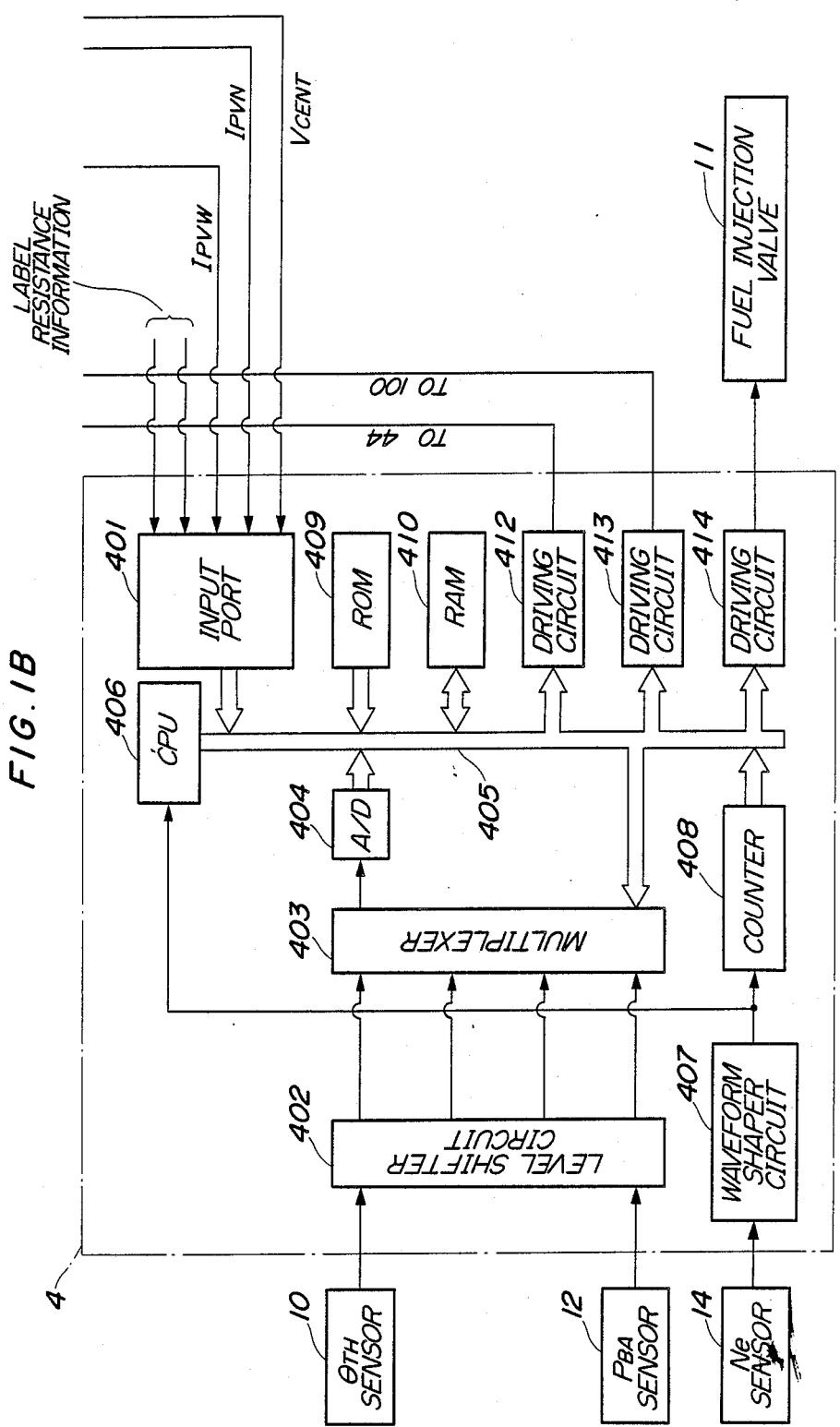

OUTPUT CORRECTION METHOD FOR EXHAUST GAS INGREDIENT-CONCENTRATION SENSORS OF PROPORTIONAL-OUTPUT TYPE

BACKGROUND OF THE INVENTION

This invention relates to an output correction method for exhaust gas ingredient-concentration sensors of a proportional-output type adapted for use in internal combustion engines, and more particularly to a method of this kind, which enables to properly correct variations in output characteristic between the individual sensors.

A method is known, in which exhaust gas concentration is sensed and the air-fuel ratio of a mixture supplied to an internal combustion engine is controlled to a desired ratio in a feedback manner responsive to the sensed concentration, so as to enhance the emission characteristics of the engine and reduce fuel consumption. As an $0_2$ sensor for sensing the concentration of oxygen contained in the exhaust gases, so called proportional-output type $0_2$ sensors are known, which generate an output proportional to the oxygen concentration.

$0_2$ sensors of this type include a limiting current type comprising a cell element and an oxygen-pumping element, each composed of a plate-like member formed of a solid electrolytic material having oxygen ion-conductivity, and a couple of electrodes attached to opposite side surfaces of the plate-like member, and which senses the air-fuel ratio of the mixture e.g. by pumping oxygen into and out of a gas diffsion chamber defined between the cell and oxygen-pumping elements.

However, there can be variations in the output value between individual $0_2$ sensors due to variations in the diameter of a gas-introducing slit opening into the gas diffusion chamber, or variations in the composition or thickness between individual solid electrolytic materials, or variations in the heating temperature or processing time for forming the materials. These variations cause variations in the air-fuel ratio value detected by the individual $0_2$ sensors.

A method for correcting such variations in the air-fuel ratio is known e.g. from Japanese Provisional Utility Model Publication (Kokai) No. 60-120354, in which a correction resistance is connected as a circuit constant to a circuit connecting the oxygen-pumping element to a power source, wherein correction of variations in the output between individual sensors is carried out by changing the amount of current flowing in the circuit by means of the correction resistance.

Further, another method for correcting the variations has been proposed by the assignee of the present application in Japanese Provisional Pat. Publication (kokai) No. 62-198744, in which when the output level of the sensor is equal to a predetermined reference value, the amount of fuel supplied to the engine is actually changed by a predetermined amount, and a correction value is calculated on the basis of a change in the output of the sensor resulting from the change in the amount of fuel, and the correction value is used to correct the sensor, thereby enabling the correction merely by means of calculation.

However, the method according to Publication No. 60-120354 has the following disadvantage: In an $0_2$ sensor which can sense the air-fuel ratio over a wide range from the rich side to the lean side with respect to a stoichiometric, the output (pumping current Ip) characteristic of the sensor is generally such that the rate of a change in the pumping current Ip responsive to a change in the air-fuel ratio on the rich side is different from that responsive to a change of the air-fuel ratio on the lean side Therefore, the sensor output cannot be properly corrected on both the rich side and the lean side by means of a single correction resistance to thereby fail to detect the air-fuel ratio with accuracy. Consequently, this method requires the use of two correction resistances to correct the sensor output on both the rich side and the lean side.

On the other hand according to the method of Publication No. 62-198744, although the correction of the sensor output can be effected by means of calculation within a microcomputer, it is required to actually change the amount of fuel by multiplying a normally required amount of fuel by a predetermined value, which will make the engine control complicated.

SUMMARY OF THE INVENTION

It is the object of the invention to provide an output correction method for exhaust gas ingredient-concentration sensors of a proportional-output type, which is capable of easily and properly correcting variations in the air-fuel ratio detected by individual sensors due to variations in output characteristic between the sensors, to thereby enhance the accuracy of detecting of the air-fuel ratio.

To attain the above object, the present invention provides a method of correcting an output of an exhaust gas ingredient-concentration sensor of a proportional-output type including at least one oxygen concentration detecting element formed by an oxygen-pumping element and a cell element, each of the oxygen-pumping element and the cell element being composed of a wall of a solid electrolytic material having oxygen ion-conductivity, and a pair of electrodes having the wall interposed therebetween, the oxygen-pumping element and the cell element defining a gas diffusion-limiting zone therebetween, current detecting means connected to the oxygen-pumping element for detecting a value of current flowing therein, voltage applying means for applying an output voltage corresponding to a differrence between a voltage developed between the electrodes of the cell element and a predetermined reference voltage to the oxygen-pumping element, and control means for calculating a desired value of an air-fuel ratio of an air-fuel mixture on the basis of the value of the current detected by the current detecting means.

The method according to the invention is characterized by comprising the following steps:

(1) supplying the control means with information indicative of a deviation of the air-fuel ratio detected by the sensor with respect to a predetermined reference air-fuel ratio;

(2) determining a correction value on the basis of the information and a direction of flow of the current;

(3) correcting the detected value of the current by the use of the determined correction value; and (4) calculating the desired value of the air-fuel ratio on the basis of the corrected value of the current.

Preferably, a single value is supplied to the control means as the information, and when the current flows in one direction, the correction value is set to a first predetermined value based on the single value, while when the current flows in the opposite direction, the correction value is set to a second predetermined value obtained by multiplying the first predetermined value by a predetermined number of times.

Specifically, the current flows in the one direction when the air-fuel ratio detected by the sensor is on one of a rich side and a lean side with respect to a stoichiometric ratio, while the current flows in the opposite direction when the detected value of the air-fuel ratio is on the other of the rich side and the lean side.

The information may be a value of at least one correcting resistance which is disconnected from the current detecting means and the voltage applying means.

The above and other objects, features, and advantages of the invention will be more apparent from the ensuing detailed description taken in conjunction with the accompanying drawings.

BRIEF DESCRIPTION OF THE DRAWINGS

FIG. 1 is a schematic diagram showing the entire arrangement of a fuel supply control system employing an oxygen concentration sensor to which the method of the invention is applied:

DETAILED DESCRIPTION

Figure 2:
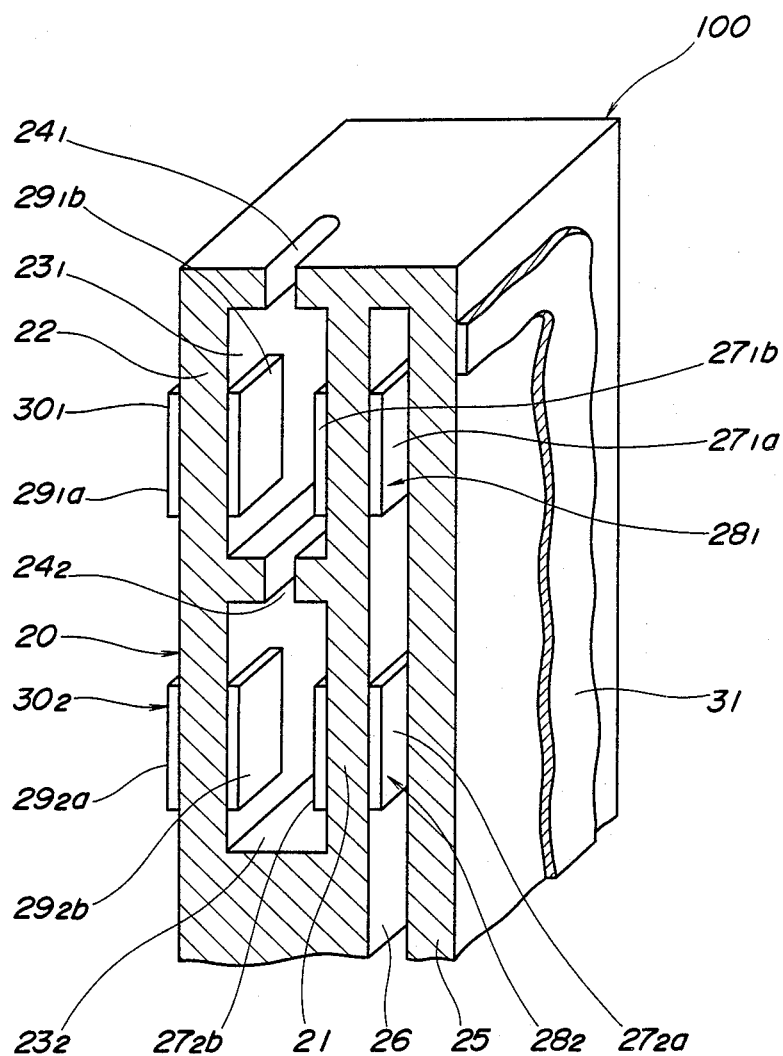
FIG. 2 is a prespective view of the sensor body of the oxygen concentration sensor in FIG. 1.

The invention will now be described in detail with reference to the drawings showing an embodiment thereof.

FIG. 1 shows the entire arrangement of a fuel supply control system employing an oxygen concentration sensor to which the method of the invention is applied.

In FIG. 1, reference numeral 100 designates a body(-sensor element section) of the oxygen concentration sensor (hereinafter called "the O$_2$ sensor") 1. The sensor body 100 is arranged within an exhaust system of an engine, not shown, in which a three-way catalyst is arranged for purifying ingredients HC, CO, and NOx contained in the exhaust gases emitted from the engine.

As shown in FIG. 2 in detail, the sensor body 100 is in the form of a rectangular parallelepiped, and comprises a basic body 20 formed of a solid electrolytic material having oxygen ion-conductivity (e.g. zirconium dioxide (ZrO$_2$).

The sensor body 100 shown in FIG. 2 is a type which has two oxygen concentration detecting elements longitudinally arranged, each having a cell element and an oxygen pumping element. The basic body 20 of the sensor body 100 has first and second walls 21, 22 extending parallel with each other, between which first and second gas diffusion chambers, 23$_1$, 23$_2$ serving as gas diffusion-limiting zones are defined.

The first gas diffusion chamber 23$_1$ is communicated with an exhaust pipe, not shown, of the engine through a first slit 24$_1$ which is disposed such that exhaust gases in the exhaust pipe can be guided into the first gas diffusion chamber 23$_1$ through the slit 24$_1$. The exhaust gases within the first gas diffusion chamber 23$_1$ is introduced into the second gas diffusion chamber 23$_2$ through a second slit 24$_2$ communicating between the two chambers 23$_1$ and 23$_2$. An air reference chamber 26 to be supplied with air or reference gas is defined between the first wall 21 and an outer wall 25 disposed adjacent the first wall 21 and extending parallel therewith.

In order to detect oxygen concentration within the first gas diffusion chamber 23$_1$, a couple of electrodes (first electrodes) 27$_1$a, 27$_1$b formed of platinum (Pt) are mounted on opposite side surfaces of the first wall 21, which cooperate with the first wall 21 to form a cell element (sensing cell) 28$_1$ for the first oxygen concentration detecting element, while another couple of electrodes 29$_1$a, 29$_a$b are similarly mounted on opposite side surfaces of the second wall 22, which cooperate with the second wall 22 to form an oxygen-pumping element (pumping cell) 30$_1$ for the first oxygen concentration detecting element.

On the other hand, in order to detect oxygen concentration within the second gas diffusion chamber 23$_2$, a cell element 28$_2$ for the second oxygen concentration detecting element having a couple of electrodes 27$_2$a, 27$_2$b, and an oxygen-pumping element 30$_2$ for the second oxygen concentration detecting element having a couple of electrodes 29$_2$a, 29$_2$b are respectively mounted on the first and second walls 21, 22, similarly to the cell element 28$_1$ and the oxygen-pumping element 30$_1$.

A heater (heating element) 31 is provided on an outer side surface of the outer wall 25, for heating the cell element 28$_1$, 28$_2$ and the oxygen-pumping elements 30$_1$, 30$_2$ to activate them.

The electrodes 27$_1$b and 29$_1$b for the first oxygen concentration detecting element, which are located on the first gas diffusion chamber 23$_1$ side, are connected with each other (in the embodiment, they are connected by a suitable electrically conductive member 32$_1$), and are connected to an inverting input terminal of an operational amplifier 41 through a line 1.

On the other hand, the other electrode 27$_1$a of the cell element 28$_1$ for the first oxygen concentration detecting element is connected to an inverting input terminal of a differential amplifier circuit 42$_1$ for the first oxygen concentration detecting element. The differential amplifier circuit 42$_1$ forms voltage applying means together with a reference voltage source 43$_1$ connected to a non-inverting input terminal thereof for applying to the oxygen-pumping element 30$_1$ a voltage corresponding to the difference between a voltage (cell element voltage) developed between the electrodes 72$_1$a and 27$_1$b of the cell element 28$_1$ (in the embodiment, the sum of a voltage on the line 1 and the cell element voltage) and a reference volta $V_{so}$ from the reference voltage source 43$_1$.

In the embodiment, the reference volta $V_{so}$ of the sum of the cell element voltage developed across the cell element 28$_1$ when the air-fuel ratio of a mixture supplied to the engine is equal to a stoichiometric mixture ratio, e.g. 0.45 volts and a predetermined reference voltage, hereinafter referred to, applied to a non-inverting input terminal of the operational amplifier 41.

The differential amplifier circuit 24$_1$ has an output thereof connected to the electrode 29$_1$a of the oxygen-pumping element 30$_1$ remote from the first gas diffusion chamber 23$_1$ by way of a switch 44$_1$ of a switching circuit 44. The switching circuit 44 is controlled to close or open in dependence on activation and non-activation of the sensor body 100 as well as on operating conditions of the engine. More specifically, when the sensor body 100 is inactivated, both of the switches 44$_1$ and 44$_2$ are opened, and on the other hand, when it is activated, one of the switches is closed in response to operating conditions of the engine.

The non-inverting input terminal of the operational amplifier circuit 41 is connected to a reference voltage source 45 to be supplied with the predetermined reference voltage therefrom. A current detecting resistance 46 for detecting pumping current Ip is connected between an output terminal of the operational amplifier circuit 41 and the line 1 or an inverting input terminal of the operational amplifier circuit 41. That, is the resistance 46 also serves as the negative feedback resistance of the operational amplifier circuit 41.

In the operational amplifier circuit 41 connected as above, provided that there is no offset in the output of the circuit 41, when the air-fuel ratio is equal to the stoichiometric ratio, no pumping current Ip flows in the line 1 and is applied to the inverting input terminal of the circuit 41 according to the input level setting for the differential amplifier $42_1$, and then the output voltage is equal to the reference potential at the non-inverting input terminal and an electric potential at the inverting input terminal is also equal to the reference potential. On the other hand, when the air-fuel ratio is not equal to the stoichiometric ratio, pumping current is supplied to the inverting input terminal, and an output voltage is generated at the output of the circuit 41, which corresponds to the amplification degree or factor (even if it is 1) determined by the value of the resistance 46. Although the output voltage varies in response to the magnitude of the pumping current Ip, the potential at the inverting input terminal is maintained at a constant value substantially equal to the reference potential at the non-inverting input terminal due to the action of the operational amplifier 41.

More specifically, with the above described construction, when no pumping current Ip flows in the line 1, i.e. Ip is zero, the output voltage $I_{PVW}$ of the operational amplifier 41 (i.e. the voltage at one end of the resistance 46) is made equal to the reference voltgage $V_{REF}$ from the reference voltage source 45, and at the same time a voltage $V_{CENT}$ applied to the inverting input terminal (i.e. the voltage in the line 1 and at the other end of the resistance 46) is made equal to the reference voltage $V_{REF}$.

Further, even when the pumping current Ip is not zero and varies within the lean side or within the rich side in response to the air-fuel ratio of the supplied mixture, as hereinafter referred to, the voltage at the inverting input terminal of the operational amplifier 41 or at the other end of the resistance 46 connected to the line 1, is made substantially equal to the voltage at the non-inverting input terminal, i.e. the reference voltage $V_{REF}$ irrespective of a change in the pumping current Ip.

As described above, the voltage $V_{CENT}$ on the line 1 and accordingly at the other end of the resistance 46 is maintained substantially at the voltage $V_{REF}$, irrespective of whether the pumping current Ip assumes zero or varies. On the other hand, the voltage at the one end of the resistance 46 connected to the output of the operational amplifier circuit 41 is varied in response to the direction of the pumping current Ip (the positive direction or the negative direction) and the amount of the current Ip. Therefore, the voltage $V_{CENT}$ is a reference value (reference voltage) for detecting current flowing through the oxygen-pumping element and calculating the air-fuel ratio based on the detected current value.

In this sense, the potential on the line 1 is not the earth potential, but the whole system including the line 1 and the current detecting resistance 46 is raised in potential from the ground level by the reference voltage $V_{REF}$. Consequently, when the pumping current Ip is determined from a potential difference between the opposite ends of the current detecting resistance 46, that is, from the respective voltages $V_{CENT}$ and $I_{PVW}$, as hereinafter described, the reference value $V_{CENT}$ as well as the other end voltage $I_{PVW}$ are always positive voltages, irrespective of whether the pumping current Ip flows in the positive direction or in the negative direction in response to the air-fuel ratio, thereby facilitating the calculation of the air-fuel ratio.

Further, the raising-up of the reference voltage of the pumping current detecting system to the constant reference voltage as above is advantageous for avoiding erroreous detecting of the current due to noise, especially high level noise such as ignition pulse noise of the engine.

The voltage $V_{REF}$ of the reference voltage source 45 of the operational amplifier circuit 41 is set at a predetermined voltage (e.g. 205 volts) also for ensuring the above described advantage.

The second oxygen concentration detecting element of the sensor body 100 has a similar construction to the first oxygen concentration detecting element. That is, in the voltage applying circuit and the switching circuit 44, there are respectively provided a differential amplifier circuit $42_2$, a reference voltage source $43_2$, and the aforementioned switch $44_2$. The switch $44_2$ is connected to the outer side electrode $29_2a$ of the oxygen-pumping element $30_2$, and the respective inner side electrodes $27_2b$ and $29_2b$ of the cell element $28_2$ and the oxygen-pumping element $30_2$ are both connected to the line 1, so that, during the use of the second oxygen concentration detecting element, the pumping current Ip flowing through the oxygen-pumping element $30_2$ flows in the line 1.

The output voltage $I_{PVW}$ of the operational amplifier circuit 41 and the voltage $V_{CENT}$ on the line 1, at the opposite ends of the current detecting resistance 46, are supplied to an input port 401 of an electronic control unit (hereinafter called "the ECU") 4 and are at the same time supplied to respective inputs of a differential amplifier circuit 47.

The differential amplifier circuit 47 amplifies the difference between the voltage $V_{CENT}$ and the output voltage $I_{PVW}$ of the operational amplifier circuit 41, and thus serves to improve the accuracy of a signal indicative of a voltage detected from pumping current Ip which assumes 0 or a value close thereto, i.e. where the air-fuel ratio is within a predetermined range about the stoichiometric air-fuel ratio of the mixture. In the differential amplifier circuit 47, the $I_{PVW}$ signal is amplified by a predetermined magnification $\alpha$, e.g. 5 times, to be produced as a voltage $I_{PVN}$.

The output voltage $I_{PVN}$ of the differential amplifier circuit 47 is obtained by the following equation, and is also supplied to the input port 401:

$$I_{PVN} = -5(I_{PVW} - V_{CENT}) + V_{CENT} \qquad (1)$$

Therefore, three voltage signals, i.e. $V_{CENT}$ as the reference voltage, $I_{PVW}$, and $I_{PVN}$ are supplied to the input port 401 for calculating the air-fuel ratio based on the pumping current Ip. Although the pumping current can be detected by using only the voltages $V_{CENT}$ and $I_{PVW}$, it can be more accurately detected by additionaly using the voltage $I_{PVN}$ when the air-fuel ratio is in the vicinity of the stoichiometric air-fuel ratio of the mixture in which the pumping current Ip assumes small values.

Figure 3:
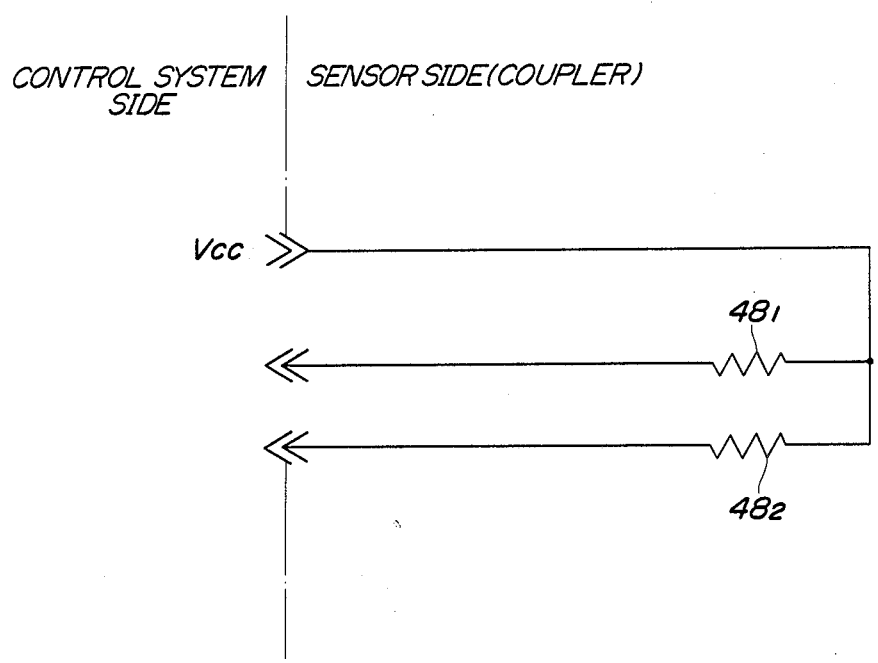
FIG. 3 is a schematic diagram showing the connection of label correction resistances to a control system for the device in FIG. 1.

Also supplied to the input port 401 is variation correcting value information for correcting variations between sensor bodies used. This information may be supplied individually for each of the first and second oxygen concentration detecting elements, if the sensor body 100 has two oxygen detecting elements as in the illustrated embodiment of the invention. Specifically, the information may be supplied by utilizing label correction resistances $48_1$ and $48_2$, as shown in FIG. 3.

The values of the label correction resistances $48_1$ and $48_2$ are set to values corresponding to variations in the characteristics of sensor bodies compared with a standard sensor body. The degree of variation in the characteristics of individual sensor body is indicated by a label indicative of its resistance value. The label correction resistances $48_1$ and $48_2$ are used together with the sensor body 100 used. That is, for instance, they maY be provide within a connecting coupler, not shown, arranged in a wire harness, not shown, connecting the sensor body 100 to the ECU 4, hereinafter referred to. When the sensor body 100 is electrically connected to the ECU 4, respective one ends of the resistances $48_1$, $48_2$ are connected to a predetermined voltage source Vcc, as shown in FIG. 3, whereby the variation correcting value information corresponding to their resistance values is inputted through the other ends of the resistances.

The input port 401 of the ECU 4 is provided therein with an A/D (analog-to-digital) converter, which converts the above-mentioned input analog signals to digital signals.

The ECU 4 is supplied with respective output signals from throttle valve opening ($\theta$th) sensor 10, and an intake pipe absolute pressure (PBA) sensor 12 as engine parameter sensors, which have then their voltage levels shifted to a predetermined level by a level shifter circuit 402 and successively applied to the A/D converter 404 through a multiplexer 403. The A/D converter 404 of the input port 401 supplies the digitally-converted data to a central processing unit (hereinafter called "the CPU") 406 via a data bus 405.

An output signal from an engine speed (Ne) sensor 14 is applied to a waveform shaper circuit 407 to have its pulse waveform shaped, and the shaped signal is supplied to the CPU 406 as a top-dead center position (TDC) signal, as well as to a counter 408. The counter 408 counts the time interval between an immediately preceding pulse of the TDC signal and a present pulse of same, inputted thereto from the Ne sensor 14. The counted value Me is proportional to the reciprocal of the actual engine rotational speed Ne. The counter 408 supplies the counted value Me to the CPU 406 via the data bus 405.

Further connected to the CPU 406 via the data bus 405 are a read-only memory (hereinafter called "the ROM") 409, and a random access memory (hereinafter called "the RAM") 4IU, and driving circuits 4I2–4I4. The RAM 410 temporarily stores results of calculations executed within the CPU 406, while the ROM 409 stores a control program to be executed within the CPU 406 for calculation of a fuel injection period $T_{OUT}$ of fuel injection valves 11, and other various programs, as well as various maps and tables.

The CPU 406 determines whether to energize or deenergize the heater 31 and whether to close or open the switches $44_1$ and $44_2$, and then supplies driving signals corresponding to the determinations to the heater 31 and the switching circuit 44 via the driving circuits $41_2$ and $41_3$.

The CPU 406 determined operation conditions of the engine such as a feedback control condition, based on the aforementioned various engine parameter signals including an output signal from the $O_2$ sensor 1, and calculates the fuel injection period of the fuel injection valves 11 in synchronism with TDC signal pulses in response to the determined engine operation conditions, based on a control program, not shown, by the use of the following equation (2):

$$T_{OUT} = T_i \times K_{02} \times K_1 + K_2 \qquad (2)$$

where Ti represents a basic fuel injection period, which is calculated from a Ti map, not shown, stored in the ROM 409, in response e.g. to the absolute pressure PBA within the engine intake pipe, and the engine rotational speed Ne. $K_{O2}$ represents an air-fuel ratio correction coefficient, which is determined in response to oxygen concentration in the actual exhaust gases, based on a control program, not shown, when the engine is in the feedback control region, while it is set to a predetermined value when the engine is in an open loop control region. $K_1$ and $K_2$ respectively represent other correction coefficients and correction variables obtained in response to various engine parameter signals, and are set to such desired values as to optimize operating characteristics of the engine such as fuel consumption and accelerability.

The CPU 406 supplies the driving signals responsive to the results of the above calculation to the fuel injection valves 11 via the driving circuit 414. The air-fuel ratio is thus feedback-controlled to a desired ratio or stochiometric ratio during the feedback operating condition of the engine.

The oxygen concentration is detected by the $O_2$ sensor in the following manner:

First, when the first oxygen concentration detecting element is selected by the switching circuit 44, as shown in FIG. 1, the exhaust gases are introduced into the first gas diffusion chamber $23_1$ through the first slit $24_1$ with operation of the engine. This causes a difference in oxygen concentration between the first gas diffusion chamber $23_1$ and the air reference chamber 26 into which air is introduced. Consequently, a voltage (sensor voltage) corresponding to the difference is developed between the electrodes $27_1a$ and $27_1b$ of the cell element $28_1$, which is added to the line 1 voltage $V_{CENT}$ and the same is applied to the inverting input terminal of the differential amplifier circuit $42_1$. As stated before, the reference voltage $V_{so}$ supplied to the non-inverting input terminal of the differential amplifier circuit $42_1$ is set at the sum of a voltage developed across the cell element $28_1$ when the air-fuel ratio is equal to the stoichiometric air-fuel ratio, and the reference voltage $V_{REF}$ supplied to the operational amplifier circuit 41.

Therefore, when the air-fuel ratio is on the lean side, the voltage between the electrodes $27_1a$ and $27_1b$ of the cell element $28_1$ lowers, while the line 1 voltage $V_{CENT}$ is maintained at $V_{REF}$, so that the sum of the voltage between the electgrodes $27_1a$ and $27_1b$ and the $V_{CENT}$ becomes lower than the reference voltage $V_{so}$. Thus, the output level of the differential amplifier circuit $42_1$ become positive, and the positive level voltage is applied to the oxygen-pumping element $30_1$ via the switch $44_1$. By applying the positive level voltage, when the oxygen-pumping element $30_1$ is activated, oxygen present within the gas diffusion chamber $23_1$ is ionized, whereby the resulting ions move through the electrode $29_1i$, the second wall 22, and electrode $29_1a$ to be emitted therefrom as oxygen gas or pumped out of the $0_2$ sensor 1. This is, the direction of flow of the pumping current Ip from the electrode $29_1a$ to the electrode $29_1b$ and flows through the current-detecting resistance 46 via the line 1. At this time, the pumping current Ip flows from the line 1 to the output side of the operational amplifier circuit 41.

On the other hand, when the air-fuel ratio is on the rich side, the sum of the voltage between the electrodes $27_1a$ and $27_1b$ of the cell element $28_1$ and the line 1 voltage $V_{CENT}$ becomes higher than the reference voltage $V_{so}$, so that the output level of the differential amplifier circuit $42_1$ becomes negative. Consequently, reversely to the above described action, external oxygen is pumped into the gas diffusion chamber $23_1$ through the oxygen-pumping element $30_1$, and simultaneously the pumping current Ip flows from the electrode $29_1b$ to the electrode $29_1a$ and flows through the current detecting resistance 46, that is, in the direction of flow of the pumping current Ip is reverse to that in the above case.

When the air-fuel ratio is equal to the stoichiometric air-fuel ratio, the sum of the voltage between the electrodes $27_1a$ and $27_1b$ of the cell element $28_1$ and the line 1 voltage $V_{CENT}$ becomes equal to the reference voltage Vso, so that the pumping-in and out of oxygen is not effected, whereby no pumping current flows (that is, the pumping current Ip is zero).

As described above, since the pumping-in and out of oxygen and hence the pumping current Ip are controlled so as to maintain the oxygen concentration in the gas diffusion chamber $23_1$ at a constant level, the pumping current Ip assumes a value proportional to the oxygen concentration of the exhaust gases on both the lean side and rich side of the air-fuel ratio of the supplied mixture.

Signals for detecting the amount of the pumping current Ip flowing through the current-detecting resistance 46, e.g. signals indicative of respective voltages $I_{PVW}$, $V_{CENT}$, $I_{PVN}$ at the opposite ends of the resistance 46 are supplied to the ECU 4.

Similarly to the first oxygen concentration detecting element, when the second oxygen concentration detecting element is used (that is, when the swich $44_2$ of the switching circuit 44 is closed, as reversely to the position shown in FIG. 1), the pumping-in and out of oxygen is controlled so as to maintain the oxygen concentration in the second gas diffusion chamber $23_2$ at a constant value, that is, the voltage between the electrodes $27_2a$ and $27_2b$ of the cell element $28_2$ is feedback-controlled to be maintained at a constant value, and at the same time the signals indicative of the voltages $I_{PVW}$, $V_{CENT}$, $I_{PVN}$ for detecting the pumping current Ip flowing during the feedback control are supplied to the ECU 4 as outputs of the second oxygen concentration detecting element.

The ECU 4 then calculates the desired air-fuel ratio based on the supplied signals and determines the value of the air-fuel ratio correction coefficient $K_{O2}$ in the aformentioned equation (2) based on the calculated desired air-fuel ratio.

Figure 4:
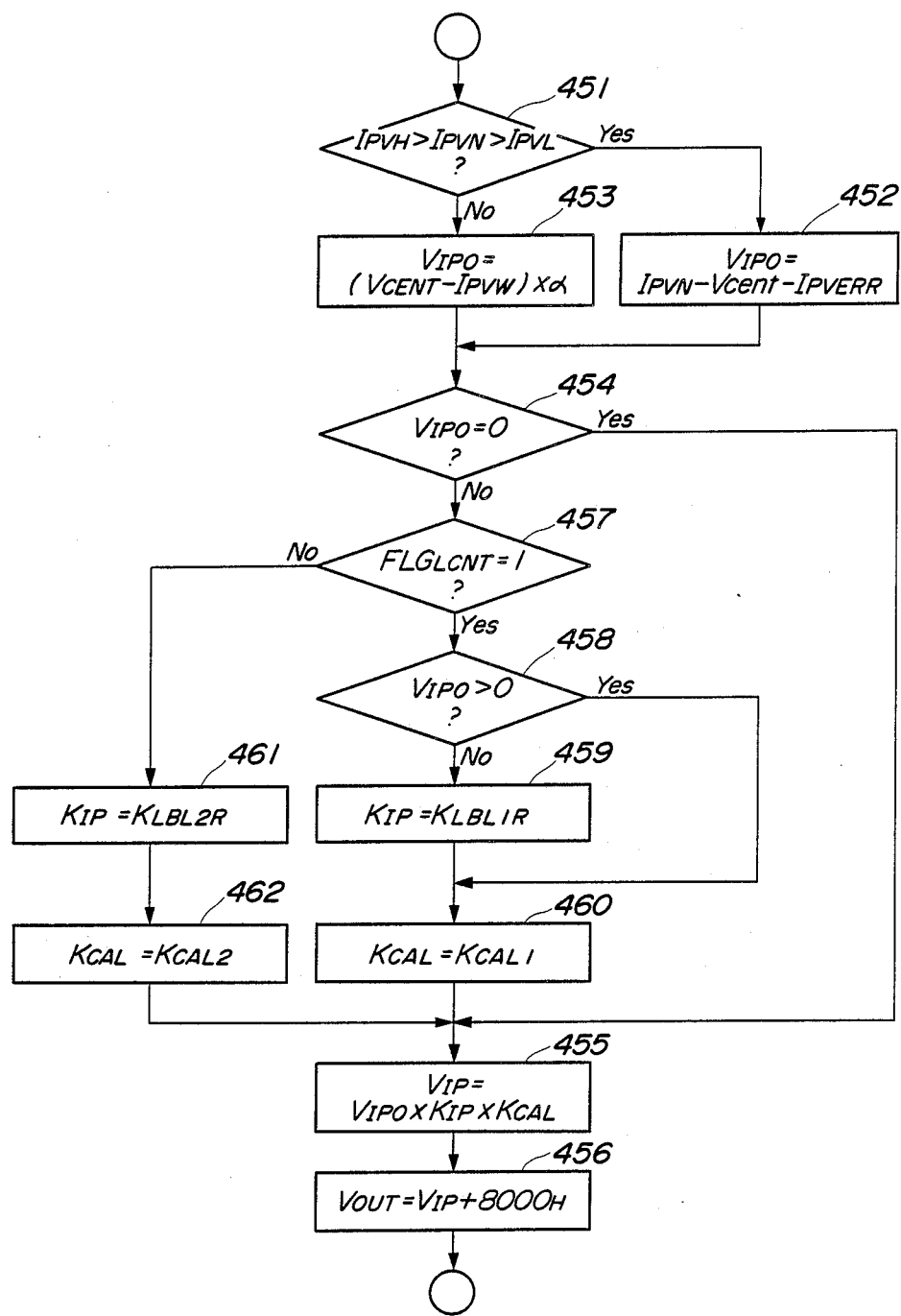
FIG. 4 is a flowchart of a subroutine for calculating a voltage value $V_{OUT}$ converted from pumping current flowing in the oxygen concentration sensor in FIG. 1.

FIG. 4 shows a subroutine for calculating an output voltage $V_{OUT}$ corresponding to the pumping current Ip, which includes a process for correcting the output of the $0_2$ sensor. This program is executed in the ECU 4 upon generation of TDC signal pulses and in synchronism therewith.

At a step 451, it is determined whether or not the output voltage $I_{PVN}$ of the differential amplifier circuit 47 is within a predetermined small value range with a middle value about which the voltage $I_{PVN}$ varies. That is, it is determined whether or not the value $I_{PVN}$ is larger than a first predetermined value $I_{PVL}$ (e.g. 2.3 volts) and at the same time smaller than a second predetermined value $I_{PVH}$ (e.g. 2.6 volt). Depending upon the answer to the question of the step 451 it is determined whether to determine a voltage $V_{IPO}$ corresponding to the pumping current Ip either by using the voltage $I_{PVW}$ which is direct output of the operational amplifier circuit 41, or by using the voltage $I_{PVN}$ which is obtained by amplifying the voltage $I_{PVW}$ by the differential amplifier circuit 47.

If the answer to the question of the step 451 is Yes, that is, if the voltage $I_{PVN}$ fulfills the condition $I_{PVH} > I_{PVN} > I_{PVL}$ (which means that the pumping current Ip assumes a small value equal to 0 or in the vicinity of 0, and that the air-fuel ratio is within a narrow range about the stoichimetoric air-fuel ratio (e.g., 14.7)), the value $I_{VPO}$ is calculated by the following equation (step 452):

$$V_{IPO} = I_{PVN} = V_{cent} = I_{PVERR} \quad (3)$$

where $V_{cent}$ represents a reference voltage for the voltage $V_{CENT}$ at the one end of the current detecting resistance 46 remote from the output of the operational amplifier circuit 41, while $I_{PVERR}$ represents a correction value for compensating for circuit errors such as the offset of the operational amplifier circuit 41.

The calculation at the step 452 is based on the following ground:

By using the voltage $I_{PVN}$ which is obtained by amplifying the voltage $I_{PVW}$ by the operational amplifier circuit 47 when the voltage $I_{PVN}$ assumes a value within the small value range of the step 452, it is possible to enhance the accuracy of calculation of the pumping current Ip. If the air-fuel ratio is changed to the lean side or to the rich side from the above small value range where the air-fuel ratio is equal to or close to the stoichiometric air-fuel ratio (14.7), such change exerts a great influence upon the purification degree i.e. conversion efficiency of the three-way catalyst. Therefore, more accuracy is required in detecting the air-fuel ratio than when the air-fuel ratio is changed within a range remote from the stoichiometric air-fuel ratio. Therefore, in order to improve the detection accuracy in an air-fuel ratio range in the vicinity of the stoichiometric air-fuel ratio, the direct output voltage $I_{PVW}$ is not directly used but the amplified voltage $I_{PVN}$ is applied to calculation of the voltage value $V_{IPO}$, which is obtained by amplifying $I_{PVW}$ by a predetermined number of times $\alpha$.

In the equation (3), the subtraction of the reference voltage $V_{cent}$ is effected for correcting the reference potential or zero potential.

As stated before, the potential of the pumping current detecting system including the current detecting resistance 46 and the operational amplifier circuit 41 is raised up by the reference voltage $V_{REF}$ to always maintain the voltages at the opposite ends of the resistance 46 at positive levels even if the direction of flow of the pumping current Ip is changed. Therefore, the voltage at the end of the resistance 46 close to the output of the operational amplifier circuit 41 varies about the reference voltage $V_{REF}$ from the reference voltage source 45, in response to the direction of flow of the pumping current Ip and the amount of the same current. Thus, the amount of the pumping current Ip can be determined from the difference between the reference voltage $V_{REF}$ and the voltage varying in response to the flow of the pumping current Ip. Therefore, at the step 452 the reference voltage $V_{cent}$ is subtracted from the voltage $I_{PVN}$.

The reference voltage $V_{cent}$ corresponds to the line 1 voltage $V_{CENT}$. If there is no circuit error in the operational amplifier circuit 41, etc., and the pumping current Ip is zero (that is, the air-fuel ratio is equal to the stoichiometric air-fuel ratio), the value $V_{cent}$ should be set to a valve equal to the reference voltage $V_{REF}$.

Therefore, by obtaining ($I_{PVN} - V_{cent}$), even if there is an error (e.g. setting error) in the voltage from the reference voltage source 45, or even if the voltage from the source 45 varies, the value ($I_{PVN} - V_{cent}$) is always zero when the actual pumping current Ip is zero. This correction enables detecting the pumping current accurately. Thus, the air-fuel ratio detection accuracy is improved especially when the air-fuel ratio is in the vicinity of the stoichiometric air-fuel ratio (14.7), in addition to the aformentioned advantage of noise proof.

Referring again to the step 452, the correction value $I_{PVERR}$ is subtracted from ($I_{PVN} - V_{cent}$), whereby the detection accuracy can be further enhanced.

Although, in the above explanation, it has been assumed that there is no circuit error such as the offset in the operational amplifier circuit 41, actually there can be such an error in the circuit 41. Especially, in the vicinity of the stoichiometric air-fuel ratio, the pumping current Ip assumes a very small value near zero, and hence the difference between the reference voltage and the voltage varying in response to the pumping current Ip becomes very small, so that such a circuit error as the offset greatly affects the accuracy of detection.

Therefore, to correct the offset in the circuit 41, the correction value $I_{PVERR}$ is subtracted from ($I_{PVN} - V_{cent}$) at the step 452.

The value $I_{PVERR}$ is obtained by executing a subroutine, not shown.

If the answer to the question of the step 451 is No, that is, if $I_{PVN} \geq I_{PVH}$ or $I_{PVN} \leq I_{PVL}$ is fulfilled, which means that the value of $I_{PVN}$ is out of the predetermined range, it is judged that the pumping current Ip has neither a value of 0 nor a small value in the vicinity of 0, that is, the air-fuel ratio is not in the vicinity of the stoichiometric air-fuel ratio (14.7). The program then proceeds to a step 453, in which the value $V_{IPO}$ is calculated by the following equation:

$$V_{IPO} = (V_{CENT} - I_{PVW}) \times \alpha \quad (4)$$

where $\alpha$ is a predetermined value. That is, when the air-fuel ratio is not in the vicinity of the stoichiometric air-fuel ratio, the voltage $I_{PVW}$ value is directly used as the terminal voltage of the current detecting resistance 46 close to the output of the operational amplifier circuit 41, to calculate the difference between the line 1 voltage $V_{CENT}$ as the other terminal voltage of the resistance 46 and $I_{PVW}$, that is, ($V_{CENT} - I_{PVW}$) to obtain the voltage $V_{IPO}$. Therefore, in order to raise up the resulting value of $V_{IPO}$ to the same level as that of the resulting value obtained at the step 452, the difference ($V_{CENT} - I_{PVW}$) is multiplied by the predetermined value.

Also in the calculation at the step 453, the voltage $V_{IPO}$ value is obtained by using the raised-up voltage $V_{CENT}$ on the line 1, that is, on the basis of the difference ($V_{CENT} - I_{PVW}$), so that potential correction is effected similarly to the step 452, whereby the voltage $V_{IPO}$ corresponding to the pumping current Ip is accurately detected irrespective of the influence of noise and an error in the reference voltage $V_{REF}$.

At a step 454, it is determined whether or not the $V_{IPO}$ value obtained at the step 452 or 453 is equal to 0, in order to judge whether or not the actual air-fuel ratio is equal to the stoichiometric ratio. If the answer is Yes, that is, if Ip is equal to zero, the program jumps to a step 455 to execute the step 455 and a step 456, followed by termination of the program.

At the step 455, the $V_{IPO}$ value obtained at the step 452 or 453 is corrected to a $V_{IP}$ value by being multiplied by a label resistance coefficient $K_{IP}$. Then at the step 456, the value $V_{IP}$ obtained at the step 455 is increased by a predetermined number, e.g. 8000 in hexadecimal notation, to obtain a value $V_{OUT}$ as the output voltage.

At the step 454, if it is determined that the value $V_{IPO}$ is zero, the value $V_{IP}$ obtained at the step 455 is also zero, and therefore, the resulting $V_{OUT}$ value at the step 456 is 8000 in hexadecimal notation. The predetermined number is a reference or middle value of the $V_{OUT}$ value When the air-fuel ratio is changed from the stoichiometric ratio to the lean side or to the rich side, the $V_{OUT}$ value is calculated by addition or subtraction of the present value of $V_{IP}$ to or from the middle value, in accordance with the $V_{IP}$ value (the $V_{IPO}$ value assumes a positive value when the air-fuel ratio is on the lean side with respect to the stoichiometric ratio, and a negative value when the latter is on the rich side, and the $V_{IP}$ value also assumes a positive value or a negative value correspondingly).

As stated above, the voltage value $V_{IP}$ obtained at the step 455 is not made the final value, but it is increased by the predetermined number at the step 456. This is for preventing the $V_{OUT}$ value from assuming a value of 0 when the air-fuel ratio is equal to the stoichiometric ratio where the pumping current Ip is 0, to thereby enable avoiding an inconvenience encountered when the $k_{O2}$ value is determined on the basis of the $V_{OUT}$ value, e.g. when the $k_{O2}$ value is obtained by division.

If the answer to the question of the step 454 is No, it is determined at a step 457 whether or not a flag $FLG_{LCNT}$ has been set to a value of 1. If the answer at the step 457 is Yes, it is determined that the first oxygen concentration detecting element in FIG. 1 is not being used, and then the program proceeds to step 458.

The flag $FLG_{LCNT}$ indicates whether the first oxygen concentration detecting element or the second oxygen concentration detecting element is being used. That is, when the first oxygen concentration detecting element is being used the value N is set to 1, while it is set to 2 when the second oxygen concentration detecting element is being used.

At the step 458, it is determined whether or not the present $V_{IPO}$ value is larger than zero (i.e. positive or negative). That is, it is determined whether the air-fuel ratio is on the lean side or on the rich side with respect to the stoichiometric ratio.

If the answer to the question of the step 458 is Yes, that is, if the $V_{IPO}$ value is positive, it is determined that the air-fuel ratio is on the lean side, and then the program proceeds to a step 460, hereinafter referred to. On the other hand, if the answer is No, that is, if the $V_{IPO}$ value is negative, it is determined that the air-fuel ratio is on the rich side, and then the program proceeds to a step 459, where the $K_{IP}$ value is set to a predetermined value $K_{LBL1R}$, followed by the program proceeding to the step 460.

The predetermined value $K_{LBL1R}$ set at the step 455 is a correction coefficient used for correcting variations in output characteristic between individual $0_2$ sensors, to be applied when the air-fuel ratio is on the rich side with respect to the stoichiometric air-fuel ratio, that is, when the pumping current Ip is below zero during the use of the first oxygen concentration detecting element.

The correction coefficient $K_{LBL1R}$ is obtained by a subroutine, not shown, wherein it is determined based on the value of the label correction resistance $48_1$ for the first oxygen concentration detecting element.

The label correction resistance $48_1$ is provided within a coupler, not shown, for obtaining the correction coefficient for the first oxygen concentration detecting element. The resistance value of the label correction resistance $48_1$, which can be obtained by detecting current flowing through the resistance $48_1$ or voltage between opposite ends thereof developed when the predetermined voltage Vcc, e.g. 5V, is applied, is set at a value corresponding to the degree of deviation of the air-fuel ratio detected by an individual $0_2$ sensor used, with respect to the resistance value of a reference $0_2$ sensor. Therefore, the correction coefficient $K_{LBL1R}$ can be obtained by detecting the resistance value of the label correction resistance $48_1$ by means of the ECU 4.

In the arrangement shown in FIG. 3, a single label correction resistance is used for each detecting element. Since the correction coefficient is set to different values in accordance with the direction of flow of the pumping current Ip (i.e. $V_{IPO}>0$ or $V_{IPO}<0$) according to the method of the invention, an example of which is shown in FIG. 4, even the use of a single label correction resistance can perform correction on both the lean and rich sides.

The method of the invention is based upon the fact that the air-fuel ratio vs. pumping current characteristic of an $0_2$ sensor of the proportional-outout type has correlation in variation between the rich side and the lean side.

Specifically, if the actual output of the sensor is, for example, deviated toward the rich side by a predetermined number of times. e.g. 1.3 times, with respect to a reference output, the actual output on the lean side is also deviated by a predetermined number of times which is correlated with the degree of deviation of the output toward the rich side.

Therefore, even in the case that the detected pumping current Ip is corrected by the use of the label correction resistance which is not connected to the voltage applying means and the pumping current detecting circuit (the resistances $48_1$ and $48_2$ are not circuit constants in the above circuits), as shown in FIG. 3, a correction value may be, for instance, determined on the rich side from the actual label correction resistance value when the pumping current Ip value is negative, while a correction value on the lean side may be determined by multiplying the correction value determined on the rich side by a predetermined number of times, or vice versa.

Thus, even a single correction resistance can enable correction on both the rich side and the lean side.

In FIG. 4, as an example, the amount of correction is made different between the lean side and the rich side in such a manner that the $K_{IP}$ value is set to a value of 1 on the lean side, while it is set to $K_{LBL1R}$ on the rich side.

The use of a single correction resistance is advantageous in the arrangement of FIG. 3 wherein the label correction resistance 48 is accommodated within the coupler, since the coupler which accommodates only one correction resistance can be made compact.

Referring again to FIG. 4, at the step 460, a deterioration correction coefficient $K_{CAL}$ is set to a predetermined value $K_{CAL1}$ for the first oxygen concentration detecting element, followed by execution of the steps 455 and 456 and then termination of the program.

The deterioration correction coefficient $K_{CAL}$ is provided for correcting a change in the output characteristic of the sensor due to a change in the flow resistance through the slit 24 caused by a reduction in the diameter of the slit with oxides contained in the exhaust gases and deposited on the inner peripheral surface thereof. The value of the coefficient $K_{CAL}$ is obtained in accordance with a subroutine, not shown. The amount of deterioration correction to be effected on the rich side is the same as that on the lean side. This correction is especially useful for enhancing the accuracy of detection of the air-fuel ratio when it is applied to the $0_2$ sensor with two oxygen detecting elements as shown in FIGS. 1 and 2.

If the answer to the question at the step 457 is No, it is judged that the second oxygen concentration detecting element is now being used. On this occasion, another label correction resistance $48_2$ for the second oxygen concentration detecting element (in FIG. 3) is used for the sensor variation correction such that the $K_{IP}$ value is set to a second predetermined value $K_{LBL2R}$ for the second oxygen concentration detecting element (step 461), and the $K_{CAL}$ value is set to a second predetermined value $K_{CAL2}$ for the second oxygen concentration detecting element (step 462). followed by termination of the program.

Although in the embodiment of the invention described as above, two oxygen concentration detecting elements are used, the invention is not limited to this, but it is also applicable to an $0_2$ sensor having a single detecting element corresponding to the first detecting element shown in FIGS. 1 and 2.

Further, a device for supplying the correction value to the ECU 4 is not limited to a coupler as used in the FIG. 3 embodiment.

Further, although in the embodiment of FIG. 4 the $K_{IP}$ value is set to 1 on the lean side and set to $K_{LBL1R}$ on the rich side, it may be set on the rich side to $K_{LBL1R}$ which is obtained based on the actual resistance value of a label resistance used, while it may be set on the lean side to $KLBL1R \times K (0 < K < 2)$.

As described above, according to the invention, the amount of correction of variations in the output characteristic of an $0_2$ sensor is varied in accordance with the direction of flow of the pumping current Ip detected for calculating the air-fuel ratio, so that the output of the sensor can be easily corrected on both the rich side and the lean side, thereby obtaining the accuracy of detection of the air-fuel ratio over the entire range of the air-fuel ratio.

What is claimed is:

1. A method of controlling the operation of an internal combustion engine in accordance with an output of an exhaust gas ingredient-concentration sensor of a proportional-output type including at least one oxygen concentration detecting element formed by an oxygen-pumping element and a cell element, each of said oxygen-pumping element and said cell element being composed of a wall of a solid electrolytic material having oxygen ion-conductivity, and a pair of electrodes having said wall interposed therebetween, said oxygen-pumping element and said cell element defining a gas diffusion-limiting zone therebetween, current detecting means connected to said oxygen-pumping element for detecting a value of current flowing therein, voltage applying means for applying an output voltage corresponding to a difference between a voltage developed between said electrodes of said cell element and a predetermined reference voltage to said oxygen-pumping element, and control means for calculating a desired value of an air-fuel ratio of an air-fuel mixture on the basis of the value of said current detected by said current detecting means, the method comprising the steps of:
(1) supplying said control means with information indicative of a deviation of the air-fuel ratio detected by said sensor with respect to a predetermined reference air-fuel ratio;
(2) setting a correction value to a first predetermined value when said current is flowing in one direction and the air-fuel ratio detected by said sensor is on one of a rich side and a lean side with respect to a stoichiometric ratio, while setting said correction value to a second predetermined value which is different from said first value when said current is flowing in an opposite direction and the detected value of the air-fuel ratio is on the other of said rich side and said lean side;
(3) correcting the detected value of said current by the use of the determined correction value;
(4) calculating said desired value of the air-fuel ratio on the basis of the corrected value of said current; and
(5) controlling the operation of the engine in response to said desired value of the air-fuel ratio calculated in step (4).

2. A method as claimed in claim 1, wherein a single value is supplied to said control means as said information, and said first predetermined value is obtained on the basis of said single value, while said second predetermined value is obtained by multiplying said first predetermined value by a predetermined number of times.

3. A method as claimed in claim 1, wherein said information is a value of at least one correction resistance.

4. A method as claimed in claim 3, wherein said at least one correction resistance is disconnected from said current detecting means and said voltage applying means.

* * * * *